United States Patent [19]

Porcher et al.

[11] Patent Number: 4,976,925
[45] Date of Patent: Dec. 11, 1990

[54] APPLIANCE DESIGNED FOR SINGLE USE FOR TAKING SAMPLES OF LIQUIDS

[75] Inventors: Alain R. Porcher, Paris; Jean-Claude Martin, Segre, both of France

[73] Assignee: Allflex Europe S.A., Paris, France

[21] Appl. No.: 295,061

[22] Filed: Jan. 6, 1989

[30] Foreign Application Priority Data

Jan. 8, 1988 [FR] France ................ 88 00156

[51] Int. Cl.$^5$ .................. G01N 1/10; G01N 33/50
[52] U.S. Cl. .................... 422/100; 73/864.02; 73/864.52; 73/864.74; 604/110; 604/202; 604/203; 128/764
[58] Field of Search ............ 422/100; 604/110, 201, 604/202, 203; 128/763, 764; 73/864.01, 864.02, 864.52, 864.74

[56] References Cited

U.S. PATENT DOCUMENTS

| | | | |
|---|---|---|---|
| 3,306,291 | 2/1967 | Barke | 604/110 |
| 3,320,954 | 5/1967 | Cowley | 604/110 |
| 4,027,669 | 6/1977 | Johnston et al. | 604/110 |
| 4,295,476 | 10/1981 | Quaas | 604/203 |

Primary Examiner—Robert J. Warden
Assistant Examiner—Lynn M. Kummert
Attorney, Agent, or Firm—Blakely, Sokoloff, Taylor & Zafman

[57] ABSTRACT

A device for single usage for sampling liquids consisting of a hollow mounting tube closed at one end by a base which has a needle mount and into which can be slid a sampling tube. The sampling tube has a cap which has a diameter in the section of the cap projecting from the tube greater than the diameter of the tube to thereby form a shoulder. The mounting tube consists of a head into which the cap of the sampling tube slides, a body to guide the sampling tube, and internally projecting studs to retain the cap in the mounting tube. A breaking point is formed where the head and body join which must be broken in order to withdraw the sampling tube from the mounting tube after a sample has been taken.

15 Claims, 2 Drawing Sheets

APPLIANCE DESIGNED FOR SINGLE USE FOR TAKING SAMPLES OF LIQUIDS

The invention consists of a device designed for single use for the taking of liquid samples.

It is known to provide devices for taking liquid samples, particularly blood, consisting of a sampling tube. This tube slides within a cylinderical mounting closed at one end by a base and fitted with a stopper which makes it watertight and slides within the tube mounting. This stopper is made of a suitable polymeric substance with a diameter slightly greater than the internal diameter of the tube mounting. The sampling tube is introduced by its cap into the tube mounting so that the cap is opposite the closed end of the tube mounting. The closed end has a needle-mounting consisting of a chamfered tube inside the tube mounting for piercing the cap and a needle mounting which projects outside the tube mounting to hold a needle. All of these have a single channel through them to carry the liquid from outside to within the tube mounting and into the sampling tube through its stopper.

To simplify operation, the sampling tube is pushed down at manufacture and kept there by the airtightness between the cap and the sampling tube.

These known devices work by piercing, with the mounting needle, at the spot from which liquid is to be drawn, pushing the tube down into the tube so a to pierce the stopper with the chamfered pin thereby causing the liquid to flow into the sampling tube because of the internal vacuum. When sufficient liquid has been drawn off, the sampling tube is drawn back in the tube mounting until the stopper comes free from the chamfered pin, so that no air can enter the sampling tube. The tube support and its needle are then immediately withdrawn.

The sampling tube is removed from the tube mounting for subsequent treatment of the liquid which it contains.

The tube mounting and its needle should then be thrown away, however many are in fact re-used with new sampling tubes. This is especially so in the veterinary area. This can lead to the spread of some diseases and can falsify subsequent analyses.

The aim of this invention is to obviate this unacceptable practice by providing a sampling device which can be used once only. This is achieved by the tube mounting being destroyed at the final stage of the liquid drawing operation.

The device consists of a hollow tube mounting closed at one end by a base which has a needle mounting into which slides a sampling tube fitted with a stopper. The diameter of the stopper in the part which extends beyond the sampling tube is greater than the tube thereby forming a shoulder partially resting on the edge of the sampling tube.

The tube mounting consists of a head into which the stopper of the sampling tube slides and a body to guide this tube. A device to retain the cap in the tube mounting is provided and it has a breaking point formed at the join between the head and the body.

The invention will now be described in detail, with a preferred non-restricting method of putting it into effect, referring to attached drawings, in which.

Figure 1:
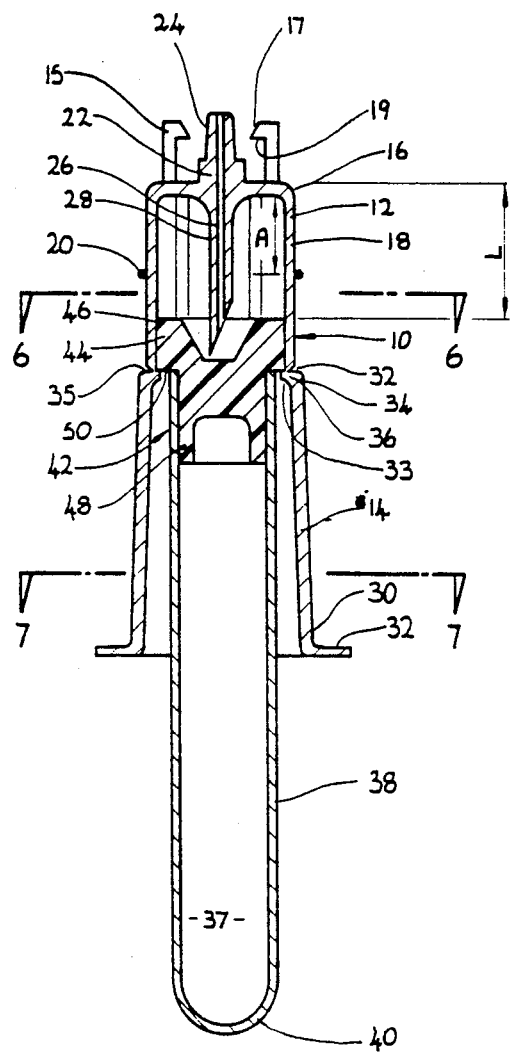
FIG. 1 is a cross-section of the sampling device according to the invention.

FIG. 1 shows a mounting tube 10 consisting of two parts, namely a head 12 and a body 14.

Figure 6:
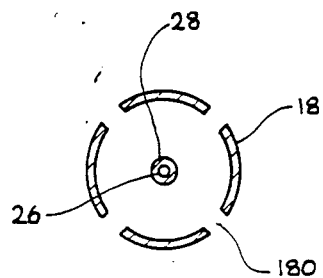
FIG. 6 shows a section through 6 to 6 in FIG. 1.

The cylindrical head 12 is made up of a base 16 and an envelope 18 with four slots 180 (see FIG. 6). Guide marks 20 are arranged externally on the envelope 18. The base has a needle mounting 22 of which one end is conical to allow a firm base for the needle and the other extends as a conical chamfered pin 26 into the head 12 of the tube mounting. This pin 26 has a greater length L than the distance separating the base 16 from the guide marks 20. A central canal 28 goes right through the needle mount. Around the needle mount is arranged a means of ratcheting the needle, made up of elastic fingers 15 fixed to the outer surface of the base 16 forming a chamfer 17 in the direction in which the needle is inserted in place and a retaining shoulder 19 in the opposite direction.

Figure 7:
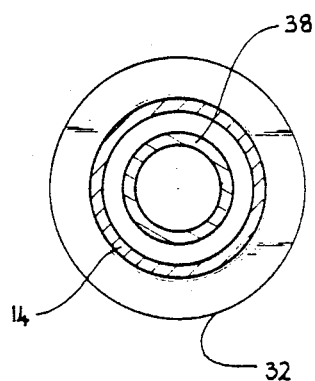
FIG. 7 shows a section through 7 to 7 in FIG. 1.

The body 14 of the tube mounting 10 is a tapering cone (see FIG. 7) and has at its open end an outer collar 32. At its end 34 in contact with the head 12 body 14 has at least two retaining studs 36. These studs are arranged on the inner surface of the body and comprise a first device which makes it easy for the cap to pass as it is being introduced, from the body towards the head, and a second device to restrain the cap 44 in the opposite direction, from the head towards the body. These devices consist respectively of a chamfer 33 going from the opening 30 towards the end 34, and of a shoulder in the opposite direction.

The head 12 and body 14 are united by a moulded joining unit consisting of at least an area of thinner material 35. The purpose of which is to enable the head 12 to be detached from the body 14 by fracturing thin areas 35.

In FIG. 1, there is shown a sampling tube 37 of given design, shape and dimensions introduced into the tube mounting as described above. This sampling tube consists of a collecting tube 38 closed at one of its ends 40 and open at the other 42. The open end 42 is stopped by an elastomeric cap 44.

Cap 44 is cylindrical and has an upper part 46 and a lower part 48, with the part 46 protruding from the collecting tube 38 of a greater dimension than the lower part 48 thereby forming a shoulder 50. The internal diameter of the tube 38 is equal to the small diameter of the cap 44, so that the shoulder of the cap 44 protudes from and engages with the end 42 of the tube 38.

Sampling tube 38 is mounted in the mounting tube 10 with the cap 44 in the head 12 and the tube guided by the body 14 as shown in FIG. 1. This position is obtained by introducing cap 44, mounted on the sampling tube 38, through the open end 30 of the body 14 of the mounting tube 10, whose diameter equals the large diameter of the cap. When pressure is applied to the closed end 40 of the collecting tube 38, the cap 44 slides into the body 14 of the mounting tube 10 and is slightly and progressively compressed because of the chamfer 33 in the reduced area of the studs 36, and thus penetrates into the head 12, where it regains its cylindrical shape and fits by sliding against the internal surface of the envelope 18, which has the same internal diameter as the cap.

The mounting tube 10 and its sampling tube 38 positioned in this way can be heat-sterilized. On cooling, the shoulder 50 of cap 44 assures that the cap is a watertight fit in the collecting tube 38, creating a slight vacuum as happens with earlier examples of devices of this type.

Figure 2:
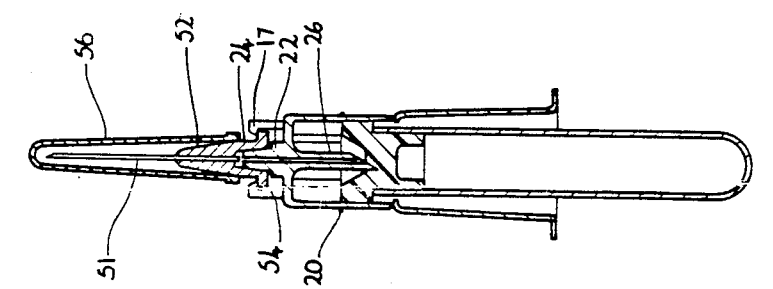
FIG. 2 is a cross-section of the device ready for use.

In FIG. 2, the mounting tube 10 and the sampling tube 38 are identical with those that have been described above, but the tube 38 has been moved in relation to the mount 10 so that the upper surface of the cap 44 comes opposite the guide marks 20, which correspond to a preliminary piercing of the cap 44 by the chamfered pin 26.

A needle 51 is in place in the needle mount 22. The shape of the base 52 of this needle is conventional and fits in an airtight fashion against the conical profile of the end 24 of the needle mount. This base consists of a flange 54 which clicks into position under the shoulders 19 of the elastic fingers 15.

A protective cap 56 is mounted on this base to protect needle 51.

Figure 3:
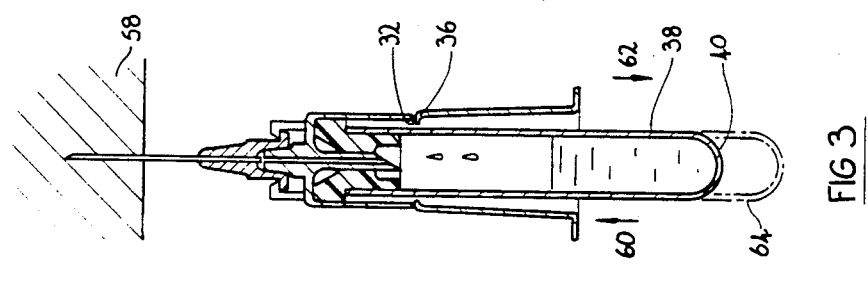
FIG. 3 is a cross-section of the device during sampling.

In FIG. 3, the device according to the invention is shown in one of the several stages of taking a sample:

The protective cap 56 is removed, the needle 51 is introduced into the medium 58 from which the sample is to be taken; immediately, by pressure on the closed end 40 of the collecting tube 38 (in the direction of the arrow 60), the cap 44 comes in contact with the base 16 of the mounting tube 10, completing the penetration of cap 44 under action of the vacuum existing in tube 38 the sample liquid flows through channel 28 and into the collecting tube 38. This is the stage shown in FIG. 3. When the desired quantity of liquid has been obtained, the sampling tube 38 is partially withdrawn in the mounting tube 10 in the direction of the arrow 62 until the shoulder 50 rests on the shoulder 32 of the studs 36, as shown in broken lines 64.

Figure 4:
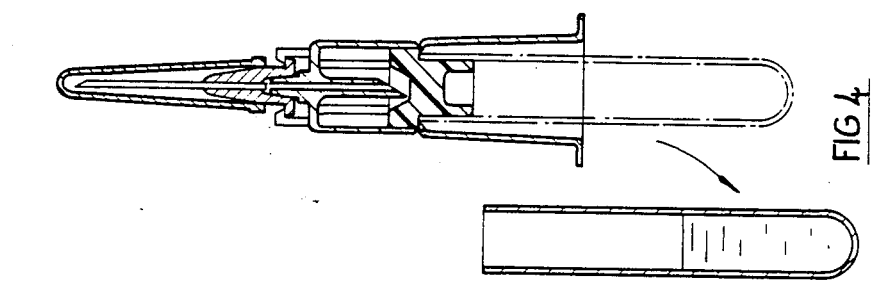
FIG. 4 is a cross-section of the device after sampling.

In FIG. 4, there is shown the result of an operator completely withdrawing the tube 38 when the cap 44 is blocked by the studs 36. The tube has come out but the cap 44 remains in the head of the tube mounting 10. Thus the sample material comes into contact with air and is no longer suitable for analysis or further use.

Figure 5:
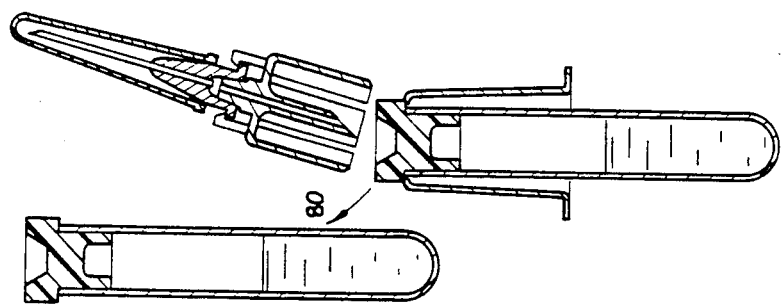
FIG. 5 shows recovery of the sampling tube and destruction of the mounting tube.

The only alternative to obtain correct usage is thus to use the device as shown in FIG. 5 and described hereunder.

The head 12 is separated from the body 14 by using the breaking point defined by the area of thinner material 35 as above described. The head 12 with its needle 51 are thrown away, and the sampling tube 38 comes out of the mounting tube 10 by moving it in the same direction as it was put in, i.e. following arrow 80. Thus it is necessary to destroy the mounting tube 10 to recover the sampling tube 38, and this guarantees a single use only.

In one variation of use, the sampling tube 38 stays in the mounting tube 10 right to the place where it will be used. When an analysis is being carried out, gloves must be worn and the work is often carried out in a glovebox. Operation is thus awkward and there can be problems in withdrawing the cap 44. The remaining section of the mounting tube 10, which is easy to grip, can thus be used to withdraw the cap with the help of the restraining studs 36.

The materials used in manufacturing such a sampling device are in particular:

an ethylene-propylene-diene-monomere elastomere (EPDM) for the cap 44, and a styrene-acrylonitrile resin (SAN for the mounting tube 10.

The collecting tube 38 is usually glass.

The invention can be carried out by more than just the method described above. For example it is possible to place an elastic retracting device between the base 16 and the upper surface of the cap 44 in the head 12 of the mounting tube 10. The elastic device compresses when the closed base 40 of the tube 38 is pushed as the sample is taken. The tube 38 thus returns to its original position automatically when the sampling is finished, with the cap once again in contact with the retaining cylinder.

In one variation, the breaking point consists of a detachable joining ring between the head and the body of the mounting tube and the two parts are separated by withdrawing this ring.

Similarly, in another variation the separate studs may become a single ring stud.

To avoid manufacturing reference marks and preliminary piercing the cap 44 may be fitted with a blind hole for the bevelled pin to enter—this reduces the thickness to be penetrated and piercing is made easier.

The device as invented is particularly aimed at taking samples of liquids such as blood and milk in the veterinary area, but could also be used on humans without any special modification.

We claim:

1. A device for single usage for sampling liquids comprising a hollow mounting tube closed at one end by a base which has a needle mount, said mounting tube slidingly receiving a sampling tube which has a cap of a diameter in a section thereof projecting from the sampling tube greater than that of the sampling tube to thereby form a shoulder which engages with an edge of the sampling tube, said mounting tube having a head portion into which the cap of said sampling tube can be slidingly engaged and a body portion to guide the sampling tube into said head portion, said mounting tube having means to retain the cap within the head portion when said cap has been located therein and thereby prevent the cap from being withdrawn from the head portion and into said body portion, the mounting tube further including means defining a frangible area whereby at least part of said head portion can be detached to permit removal of said cap from said head portion and thereby removal of said cap and sampling tube from said mounting tube.

2. Device according to claim 1 wherein the frangible area is formed where the head and body portion join.

3. Device according to claim 1 wherein the frangible area is formed where the head and body portion join and the retaining means is located adjacent to the frangible area.

4. Device according to claim 2 or 3 wherein the retaining means includes a first part to assist passage of the cap when being inserted from the body portion into the head portion, and a second part to prevent the cap from being withdrawn from the head portion and into the body portion.

5. Device according to claim 4 wherein the first part is a surface inclined toward the head portion and the second part is a shoulder.

6. Device according to claim 2 or 3 wherein the retaining means is formed by a plurality of studs located on and projecting from an inner wall of the mounting tube and with which the shoulder of the cap is engageable.

7. Device according to claim 2 or 3 wherein the head portion is of cylindrical shape and includes at least one longitudinally directed slot in the wall thereof and the body portion is of truncated conical shape and tapers toward the area where the head and body portion join.

8. Device according to claim 1 wherein the needle mount includes emans for engaging with a needle said engaging means comprising a plurality of elastic fingers forming an inclined surface in the direction in which the needle is moved to fit on the needle mount and a retaining shoulder preventing movement of the needle in the opposite direction.

9. In combination a device for single usage for sampling liquids and a sampling tube, said sampling tube having a cap which has a diameter in a section thereof projecting from the sampling tube greater than that of the sampling tube to thereby form a shoulder which engages with the edge of the sampling tube, said device comprising a hollow mounting tube closed at one end by a base which has a needle mount, said mounting tube having a head portion in which the cap of said sampling tube is slidingly engaged, said mounting tube further having a body portion to guide said cap into the head portion when the sampling tube is inserted into said mounting tube, said mounting tube having means to retain the cap within the head portion, and means defining a frangible area being provided with the mounting tube whereby at least part of said head portion can be detached to permit removal of said sampling tube from said mounting tube.

10. The combination according to claim 9 comprising means providing vacuum in the sampling tube.

11. The combination according to claim 10 wherein the frangible area is formed where the head and body portions join and the retaining means is located adjacent to the frangible area.

12. The combination of claim 10 or 11 wherein the head portion is of cylindrical form and includes at least one longitudinally directed slot in the wall thereof and the body portion is of truncated conical shape tapering toward the area where the head and body portion join.

13. The combination of claim 12 wherein the frangible area is formed where the head and body portions join and, wherein the retaining means includes a first part to assist passage of the cap, when being inserted from the body portion into the head portion, and a second part to prevent the cap from being withdrawn from the head portion into the body portion.

14. The combination of claim 13 wherein the first part is a surface inclined toward the head portion and the second part is a shoulder.

15. The combination of claim 10 or 11 wherein the needle mount includes means for engaging with a needle said engaging means comprising a plurality of elastic fingers forming an inclined surface in the direction in which the needle is moved to fit on the needle mount and a retaining shoulder preventing movement of the needle in the opposite direction.

* * * * *